United States Patent [19]

Dardik

[11] Patent Number: 5,007,430
[45] Date of Patent: Apr. 16, 1991

[54] RHYTHMIC BIOFEEDBACK TECHNIQUE

[76] Inventor: Irving I. Dardik, R.D. 1, Box 253 Hillcrest Dr., Great Meadows, N.J. 07838

[21] Appl. No.: 927,176

[22] Filed: Nov. 5, 1986

[51] Int. Cl.$^5$ .............................................. A61B 5/04
[52] U.S. Cl. .................................. 128/696; 128/707; 128/905
[58] Field of Search ............... 128/1 C, 363, 690, 696, 128/706, 707, 905; 272/99, DIG. 5, DIG. 6, DIG. 9, 73

[56] References Cited

U.S. PATENT DOCUMENTS

| | | | |
|---|---|---|---|
| 3,518,985 | 7/1970 | Quinton | 128/707 |
| 3,675,640 | 7/1972 | Gatts | 272/DIG. 6 |
| 3,802,698 | 4/1974 | Burian et al. | 128/707 |
| 4,358,105 | 11/1982 | Sweeney, Jr. | 272/73 |
| 4,436,097 | 3/1984 | Cunningham | 128/707 |
| 4,613,129 | 9/1986 | Schroeder et al. | 272/73 |

*Primary Examiner*—Francis Jaworski
*Assistant Examiner*—G. Manuel
*Attorney, Agent, or Firm*—Michael Ebert

[57] ABSTRACT

A rhythmic biofeedback technique for inducing relaxation to counteract the adverse physiological and psychological effects of chronic stress on an individual. In this technique, the heart beat of the individual being treated is continuously monitored and the prevailing rate is displayed to him as he undergoes a rhythmic conditioning session constituted by successive exercise-relaxation cycles extending for a predetermined period. In the course of each cycle, the individual is required to raise his level of exertion, as indicated by his perceived heart beat rate, to a peak representing an established safe upper limit, following which he is required to decrease his exertion until he reaches a lower limit at which a recovery relaxation response takes place. The upper and lower limits are determined by the individual's existing capacity for exercise and define his target heart rate zone.

5 Claims, 1 Drawing Sheet

RHYTHMIC BIOFEEDBACK TECHNIQUE

BACKGROUND OF INVENTION

1. Field of Invention

This invention relates generally to biofeedback therapeutic techniques, and in particular to a rhythmic biofeedback technique adapted to induce beneficial relaxation through exercise, and to a system for carrying out this technique.

2. Status of Prior Art

An individual's ability to mentally control certain of his physiological functions such as body temperature or blood pressure is known as self-regulation. For hundreds of years in the Far East, Yogis and Zen Buddhists have practiced the art of self-regulation. But with the exception of those committed to transcendental meditation, self-regulation techniques have not been widely practiced in Western society, possibly because many disorders induced or aggravated by stress which lend themselves to alleviation by self-regulation can more readily be treated by medication. Thus, a muscle contraction or tension headache as well as migraine, a vascular headache that is more painful than a tension headache, can, to some degree, be relieved by aspirin and other drugs. Such medication does not do away with stress factors responsible for the headache but serves only to moderate the symptoms. Moreover, aspirin and other drugs, when taken frequently and in large doses, often have deleterious side effects.

In recent years, biofeedback techniques have been developed which represent a more effective form of self-regulation. In biofeedback, an involuntary or unconscious physiologic process, such as the heart beat or the brain wave, is made perceptible to the senses, thereby making it possible for the individual to manipulate the process by conscious mental control Stress is expressed in many ways, and may be manifested by a headache or by high blood pressure Of overriding importance in stress therapy is learning to relax and thereby reduce tension and its physiological consequences. With biofeedback, one is able to achieve mental and physical relaxation by being fed back information regarding an unconscious physiological process. This information is derived by means of a non-invasive sensor which measures peripheral skin temperature or skin resistance, heart rate, blood pressure, pulse rate, and some other process variable.

Thus, a signal from an electromyograph is indicative of varying levels of muscular activity; the higher the signal amplitude, the greater the amount of muscular tension. A high level of muscular tension reflects a high degree of stress, giving rise to tension headaches, facial pain and tics, and other stress-related illnesses. By means of a biofeedback system, one can monitor a specific physiologic process and derive therefrom a visible or audible signal indicative of the process. In this way, the user can manipulate the process being monitored by learning to control the signal it yields. By biofeedback one can reduce muscle tension, slow down a rapid heart rate, regulate blood flow to alleviate circulatory problems and, in general, relax the nervous system.

The efficacy of biofeedback is well established. Thus, in the article by Sidney Leber, M. D., "Biofeedback in Clinical Psychiatric Practice" appearing in *Psychiatric Opinion* of October 1979, the author states that patients previously dependent on medication for migraine and other stress-related conditions which are responsive to feedback "can reduce their medications to a line of last defense rather than continue to routinely ingest medications as a way of life."

The difficulty experienced with existing biofeedback systems is that they require a fairly long training period before the user can obtain beneficial effects. The reason for this is that internal stress conditions are not a constant; and when the user first turns on his unit, he may then be in a fairly relaxed state. The unit therefore lacks, as it were, a primer; for unless the user is in a state of stress, he has nothing to work against for purposes of stress management.

SUMMARY OF INVENTION

The main object of this invention is to provide a biofeedback therapeutic technique in which physiological relaxation is induced through exercise, the technique (hereafter referred to as the rhythmic biofeedback technique) being founded on the premise that exercise and the recovery therefrom entail physiological processes that effectively correspond to stress and relaxation.

More particularly, an object of this invention is to provide a rhythmic biofeedback technique of the above type in which an individual is required to undergo a cyclical exercise and relaxation program in which a heart-rate controlled exercise functions as a stressor and the complementary relaxation interval is exploited as an "active" relaxation process.

Briefly stated, these objects are obtained by a rhythmic biofeedback technique for inducing relaxation to counteract the adverse physiological and phychological effects of chronic stress on an individual. In this technique, the heart beat of the individual being treated is continuously monitored and the prevailing rate is displayed to him as he undergoes a rhythmic conditioning session constituted by successive exercise-relaxation cycles extending for a predetermined period. In the course of each cycle, the individual is required to raise his level of exertion, as indicated by his perceived heart beat rate, to a peak representing an established safe upper limit, following which he is required to decrease his exertion until he reaches a lower limit at which a recovery relaxation response takes place. The upper and lower limits are determined by the individual's existing capacity for exercise and define his target heart rate zone.

OUTLINE OF DRAWING

For a better understanding of the invention as well as other objects and further features thereof, reference is made to the following detailed description to be read in conjunction with the accompanying drawing, wherein.

DESCRIPTION OF INVENTION

Figure 1:
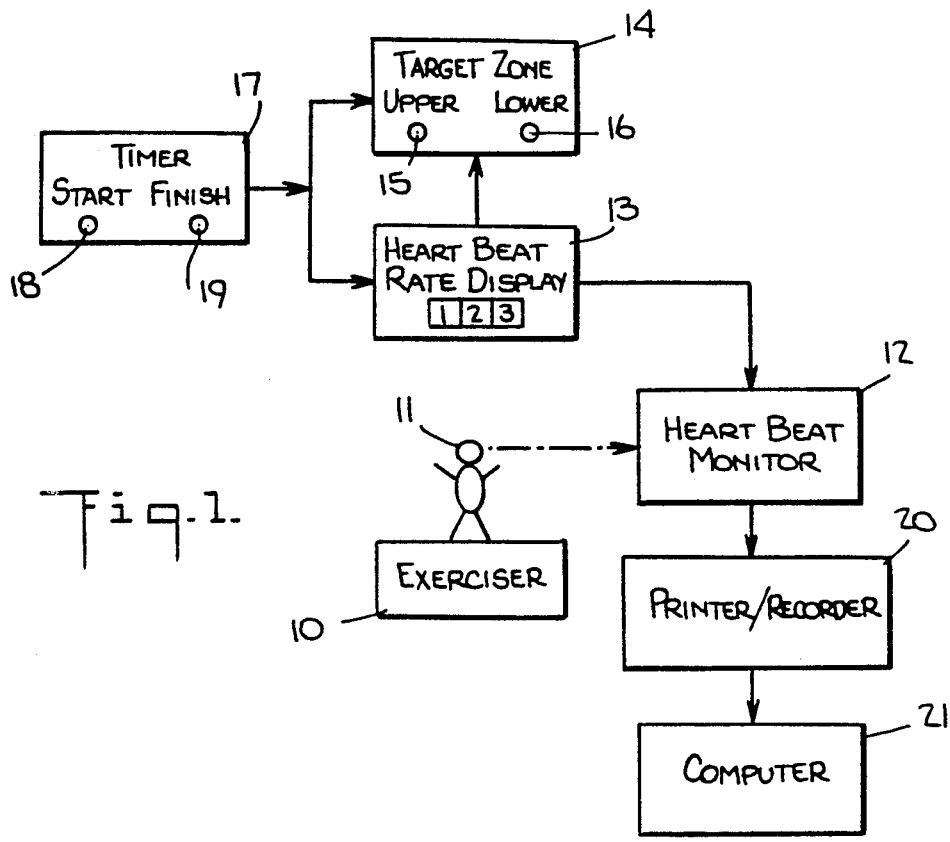
FIG. 1 is a block diagram of a system for carrying out a rhythmic biofeedback technique in accordance with the invention.

Exercise constitutes a form of stress analogous to the fight-or-flight response described by Walter Cannon. It is comprised of a cascade of well-orchestrated physiological events that undoubtedly evolved as an emergency mechanism, used by our ancestors to survive in the harsh environment in which they lived. Increased heart rate and respiratory rates result in greater oxygen consumption. This autonomic nervous system response, coupled with increased availability of glucose through activation of the hypothalmic-pituitary-adrenal axis, primes the body to cope with life-threatening events or any challenge. Homeostasis is restored when the perceived threat ceases to exist or is otherwise controlled. This recovery-relaxation response evolved as a protective mechanism designed to deactivate the fight-or-flight response.

Modern man has to a substantial degree succeeded in harnassing the environment and in so doing has reduced life-threatening stressors to a minimum. However, as is well known, the fight-or-flight response does not require the stress of a physical emergency to set it off but rather can be triggered by the everyday tensions and anxieties encountered in our modern world. These stressful events can vary from the daily ritual of contending with rush hour traffic to taking tests or having an argument with one's employer.

Over time these low-grade stressors constitute chronic insidious events from which many individuals have no escape. Physically, there is no one to fight and no place to run. Consequently, the body seeks to adapt by establishing new set-points of hormonal responsiveness on an almost continuous basis. There is little opportunity for the body to learn recovery and practice the recovery process. The new low-grade levels of tension are easily perceived by the individual as the norm. Without physical activity to raise the sympathetic nervous system response to clearly perceptible levels, it becomes difficult to master the adaptive process of the recovery-relaxation response Our growing incidence of chronic stress-related disease appears to be a consequence not only of our inability to cope with stressors but also of our inadequate use of stress. The lack of opportunity in our civilized society to take full advantage of the active component of the fight-or-flight response with its complementary recovery process, makes it difficult for us to perceive and use the adaptive process of recovery In a sense, the physiologic changes associated with recovery and relaxation have become atrophic, much as a muscle atrophies with disuse.

Currently there are numerous techniques for inducing relaxation to counter the physiological and psychological effects of chronic stress. Some examples are: progressive relaxation, yoga, autogenic training, structural integration transcendental meditation, muscle biofeedback, and sensory deprivation flotation tanks. The purpose of these essentially meditative techniques is to deactivate the sympathetic nervous system, to slow things down and to turn inwards. To develop a unified methodology around these meditative approaches, Herbert Benson in his "The Relaxation Response"; Avon Books, 1976 has synthesized four essential preconditions necessary to elicit the "relaxation response":
1. Select a quiet environment;
2. Assume a comfortable position;
3. Focus on a fixed point-usually a sound or object;
4. Assume a passive attitude.

Entering a passive state is the most important principle involved in the relaxation response. It is this inherent passivity that is difficult for many people to embrace. Unfortunately, our ability to accept modern-day stress far exceeds our ability (or willingness) to accept the meditative techniques to counter it.

The most significant contrasting principle of a rhythmic exercise-relaxation biofeedback technique in accordance with the invention resides in the use of an "active" process to induce relaxation. Whereas meditation distances itself from stress, the present invention actually exploits stress to achieve relaxation and to gain therapeutic benefits therefrom.

FIG. 1 illustrates a system for carrying out the rhythmic biofeedback technique. The system includes an exerciser 10 which in practice may take the form of a stationary bicycle, a treadmill, a rowing machine or any other exercising device which when operated by its user causes the user to more or less exert himself and thereby cause his heart to beat at a rate which is a function of this exertion.

An individual 11 undergoing exercise is coupled magnetically or by other means which are preferably wireless and therefore do not interfere with the exercise, to a heart beat monitor 12. This may be of any commercially available type capable of continuously monitoring an individual's heart beat to provide a reading of the prevailing heart beat rate on a display 13. This display may be of the digital electronic type or in any other readable form. Display 13 is so placed relative to exerciser 10 that it can be viewed by the individual. Thus in the case of a stationary bicycle, the display may be mounted on the handlebar.

Thus as the individual undergoes exercise he can see the effect of his exertion on his heart beat as in any biofeedback system. But in a rhythmic biofeedback technique, in accordance with the invention, the individual's responsive actions are governed by a program to be later explained.

Heart beat rate display 13 is coupled to a target zone detector 14 which when the prevailing rate reaches a settable upper limit, this activates an upper limit indicator 15 which may be a red LED indicator. When the rate drops to a settable lower limit this activates a green LED, lower limit indicator 16. The upper and lower limits define a target zone within which the individual must operate in the course of a conditioning session.

The duration of this conditioning session is determined by an adjustable timer 17 which enables the heart rate display 13 and the target zone detector 14. At the start of a conditioning session timer 17 turns on the display 13 and target zone detector 14 to activate the system, this start up being indicated by a "start" pilot light 18. At the conclusion of the session timer 17 turns off display 13 and zone detector 14, this being indicated by a "finish" pilot light 19.

The output of heart beat monitor 12 is also applied to a printer-recorder 20 to graphically record the successive rhythmic exercise and relaxation cycles which occur in the course of a timed conditioning session. The output of recorder 20 is digitized and applied to a digital computer 21 in which records of successive sessions are stored and diagnosed to provide an analysis of the improvements experienced by the treated individual.

Exercise, artificially recreating the fight-or-flight response, is accompanied by increased heart rate, rapid respiration, elevated blood pressure, greater blood flow to the heart and muscles, and increased lactate production. It is also accompanied by elevated levels of glucocorticoids and circulation catecholamines. Contrariwise, a decrease in the intensity of exercise is associated with a reduced level of activity in the autonomic nervous system. This recovery phase is similar to the changes associated with the (passive) relaxation response—a decrease in heart rate, a slower respiratory rate, a reduction in blood pressure, and a decline in circulating catecholamines and lactate—except that sympathetic activation is much greater after exercise.

There are four essential preconditions to using the present technique to achieve physiological relaxation:
1. Exercise;
2. Knowing one's target heart rate;
3. Rhythmic repetition of exercise and relaxation;
4. Perceived level of exertion and relaxation.

The present technique is based on a program that places equal emphasis upon both exercise and exercise-induced relaxation, accompanied throughout by the awareness of one's heart rate. Instead of exercising continuously for a particular time or distance, the technique is performed within an individual's target heart-rate "zone." This zone is determined by subtracting one's age from 220 and then multiplying the result by 70 percent to establish the lower limit of the zone and 85 percent to establish the upper limit. (For sedentary people, the percentages are 50 and 65.) It takes six to ten minutes to warm up and get into one's zone. Any type of exercise can be used as long as the heart rate is maintained in the target zone appropriate to the individual's needs (See Dardik et al. "Quantum Fitness"; N.Y. Pocket Books, 1984) After achieving the upper limit of the target zone, the recovery phase is begun by physically slowing down until the heart rate reaches the lower limit of the target zone. (Heart rate is measured by a monitor 12). This cycle is achieved within a few minutes and is then rhythmically repeated.

The average length of each conditioning session ranges from 10 to 50 minutes, and contains perhaps eight to sixteen cycles. As conditioning improves over time, a person's program can be adjusted with respect to intensity, duration, and frequency, to achieve optimal aerobic and relaxation-elicited benefits. (One can also do short reinforcing sessions at any time during the day.)

Figure 2:
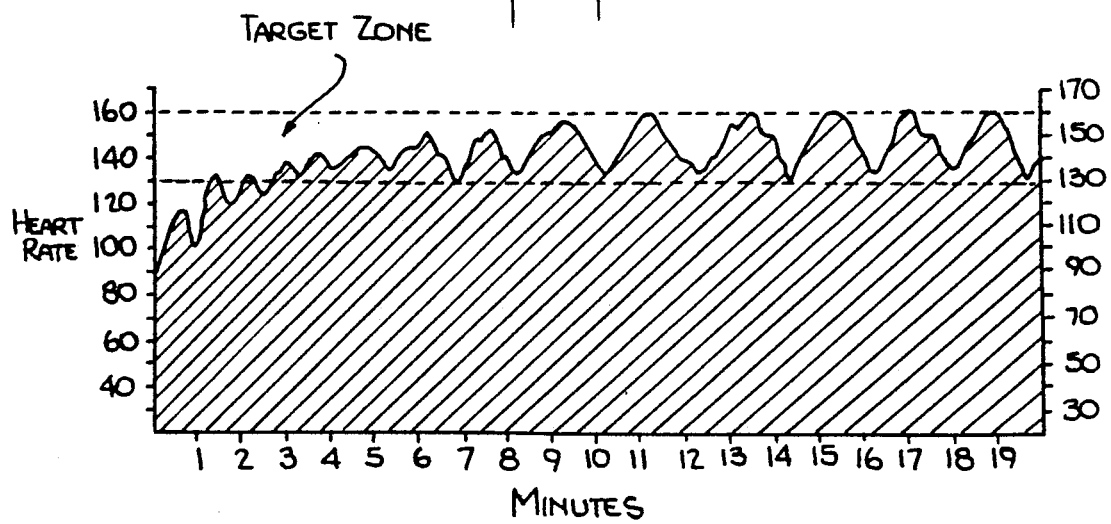
FIG. 2 is a graph showing rhythmic exercise and relaxation is a target heart zone.

FIG. 2 graphically shows the results of a conditioning session running twenty minutes in which rhythmic exercise and relaxation is cyclically carried out in a target heart zone whose lower limit is a heart beat of 130 and whose upper limit is a heart beat of 160.

Of central importance is the individual's perceived awareness of the relaxation that is actively achieved, an awareness that provides the opportunity to control the process of recovery and adaptation. By using the steering action of the heart rate, the individual is able to regulate the internal events, mediated by the autonomic nervous system, characteristic of relaxation. Thus, during the recovery relaxation response, the cardiovascular and immune systems are being trained to adapt to the physiological changes associated with stress, in much the same way that muscles are trained to become stronger with an increasing work load. This response likely occurs at the cellular level as well.

It is further hypothesized that repeated exposure to the controlled incremental release of stress-hormones followed by periods during which recovery is allowed, enables the cells of the body to respond more adequately when an individual experiences unexpected stressors. Numerous biological processes are adversely affected by major stressors for which most people have inadequate coping skills. Consider the stress of strenuous continuous exercise, which results in an outpouring of catecholamines, especially norepinephrine, that have been associated with an increase in post-exercise cardiac morbidity. (See Dimstale et al.; Postexercise; April JAMA, 1984; 351: 630-632). It is postulated that with repeated exposure to incremental doses of exercise and recovery, adaptive control of the release of catecholamines will occur, and, further, the cardiovascular system will respond more efficiently to catecholamine release. Training the recovery-relaxation response may therefore reduce the incidence of post-exercise sudden death.

An excessive amount of stress-produced catecholamines and adrenal glucocorticoids also have adverse effects on the immune system. Laboratory animals subjected to stress manifest suppressed immune activity and an increased susceptibility to opportunistic infections. Similar correlations have been made in descriptive studies using human subjects. (See Hall et al. "Thinking Well"; The Sciences; March, 1986; 30–41). It is hypothesized that the training accomplished through rhythmic biofeedback could make the cardiovascular and immune systems better able to respond to major stress-inducing events.

Instead of the fatigue typically experienced with continuous exercise, the rhythmic biofeedback technique, by incorporating the recovery-relaxation response, is enjoyable and therefore results in a high compliance rate. A sense of well being has occasionally been experienced during exercise. (This has been attributed to the release of endogenous opioids during exercise.) Individuals using the rhythmic technique routinely perceive an increasing sense of well being during each successive recovery-relaxation response. Consequently the cycles of exercise-stress and recovery-relaxation are a method of controlling "runner's high."

There is information indicating that the heightened awareness that occurs during each recovery period is also conducive to improved learning and creativity. Further, it appears that people can more easily engage in guided imagery during periods of active relaxation. Additionally, the accomplishments of athletes who use rhythmic biofeedback as part of their training regimen suggest that the program may also enhance athletic performance. In short, by rhythmically interspersing periods of relaxation (recovery) with periods of stress (exercise), an individual may be able to enhance fitness and performance while training the cellular components of the body to adapt to various types of stressors.

Rhythmic biofeedback constitutes a model for scientific inquiry into the physiological and psychological events accompanying stress and also into the subsequent ability of the body to adapt to these events. Research areas for which it could serve as a valuable model include, but are not restricted to, the study of immunology, reparative processes, aging, nutritional biochemistry, cancer, and cardiovascular rheology. More broadly, it is ideally suited for the study of interactive mechanisms between health, disease, and fitness.

While there has been shown and described a preferred embodiment of a rhythmic biofeedback technique, it will be appreciated that many changes and modifications may be made therein without, however, departing from the essential spirit thereof.

In practice, one may incorporate the entire system, save for recorder 20 and computer 21 into a compact wrist watch format, using integrated circuit chips for this purpose. In this way the individual being treated can wear the system on his wrist and observe the heart beat rate display as he exercises.

In this wrist borne system, the upper and lower limit indicators are preferably in audible form so that when the upper limit in the target zone is reached, this is announced by an audio signal that pulses at a distinct high-frequency repetition rate, and when the lower limit is reached, the signal then pulses at a much lower rate, so that it is readily distinguishable from the upper limit signal. Thus the user as he exercises need not look at his wrist, but has only to listen for the upper and lower limit signals which define each exercise cycle.

In this arrangement, in order to make it possible to get the limits of the target zone and also the duration of the timing period, switch buttons are provided as in a multi-mode digital watch to place the digital heart beat display (LCD stations) in a target zone limit adjustment mode or in a time period adjustment mode. Hence the necessary settings can be made when viewing the digital display.

I claim:

1. A rhythmic biofeedback technique for inducing relaxation to counteract the adverse physiological and psychological effect of chronic stress on an individual of a given age and physical condition, the technique comprising the steps of:

A. electronically monitoring the heart beat of an individual being treated and displaying the prevailing rate to him as he undergoes a rhythmic conditioning session constituted by successive exercise-relaxation cycles extending for a predetermined period, each cycle having a duration which is a small fraction of said period;

B. electronically producing a first indication when the prevailing rate reaches a peak representing a predetermined safe upper limit and electronically producing a second indication when the prevailing rate reaches a predetermined acceptable lower limit, said predetermined upper and lower limits defining a target heart rate zone for the particular individual being treated, the boundaries of this zone being a function of the individual's age and physical condition; and C. in the course of each cycle of the conditioning session requiring the individual to operate within said target zone by raising his level of exertion, as indicated by said first indication, to a peak representing said safe upper limit, following which he is required to reduce his exertion until he reaches said acceptable lower limit as indicated by the second indication at which a recovery-relaxation response takes place.

2. A technique as set forth in claim 1, further including this step of recording the successive cycles of each session to provide a reading of the session.

3. A technique as set forth in claim 1, further including the step of adjusting the timing period of the session and indicating the start and finish thereof.

4. A technique as set forth in claim 2, further including the step of transferring the readings of successive sessions to a computer in which these readings are stored and diagnosed to analyze the progress made by the individual being treated.

5. A technique as set forth in claim 1, wherein the individual being treated is either physically active or sedentary, and wherein the boundaries of the target zone are determined by subtracting the individual's age from 220 and then multiplying the result by 70 percent to establish the lower limit of the zone and by 85 percent to establish the upper limit of the zone for a physically active individual, the percentages being 50 and 65, respectively, for a sedentary individual.

* * * * *